United States Patent [19]

Oswald et al.

[11] 4,115,482
[45] Sep. 19, 1978

[54] STEREOSPECIFIC CIS- AND TRANS-VINYLIC PHOSPHORUS ESTERS

[75] Inventors: Alexis A. Oswald, Mountainside, N.J.; Joseph H. Lesser, Woodside, N.Y.

[73] Assignee: Exxon Research and Engineering Company, Linden, N.J.

[21] Appl. No.: 785,034

[22] Filed: Apr. 6, 1977

Related U.S. Application Data

[63] Continuation of Ser. No. 371,811, Jun. 20, 1973, abandoned, which is a continuation of Ser. No. 846,244, Jul. 30, 1969, abandoned.

[51] Int. Cl.$^2$ .......................... C07F 9/165; A01N 9/36
[52] U.S. Cl. .................... 260/957; 260/941; 260/971; 260/989; 424/219
[58] Field of Search ........................................ 260/957

[56] References Cited

U.S. PATENT DOCUMENTS

| 3,021,352 | 2/1962 | Miller | 260/957 X |
| 3,068,271 | 12/1962 | Tieman | 260/957 X |

Primary Examiner—Anton H. Sutto
Attorney, Agent, or Firm—Ernest A. Forzano; Albert P. Halluin

[57] ABSTRACT

Vinylic thiophosphorus acid esters of either cis- or trans-configuration can be synthesized in a stereospecific reaction of a cis- and a trans-vinylic metal compound with diorgano phosphoryl disulfide and a diorgano phosphoryl sulfenyl halide, respectively, and the product can be isomerized to the thermodynamically more stable mixture of isomers by free radical and ionic catalysts. The new cis- and/or trans-vinylic thiophosphorus esters are mainly useful in the field of plant and animal pesticides.

11 Claims, No Drawings

STEREOSPECIFIC CIS- AND TRANS-VINYLIC PHOSPHORUS ESTERS

This application is a continuation of Ser. No. 371,811, filed June 20, 1973, which is a continuation of Ser. No. 846,244, filed July 30, 1969, both now abandoned.

BACKGROUND OF THE INVENTION

1. Field of the Invention

This invention relates to the synthesis and isomerization of cis- and trans-vinylic thiophosphorus acid esters and to their use.

Firstly, this invention relates to the stereospecific synthesis of cis- and trans-vinylic thiophosphate, thiophosphonate and thiophosphinate esters by reacting the corresponding vinylic alkali metal or Grignard compound with the corresponding phosphoryl disulfide or phosphoryl sulfenyl chloride.

Secondly, this invention relates to the isomerization of the above cis- and trans-vinylic phosphorus acid esters to the thermodynamically more stable mixture of geometrical isomers by free radical type chemical catalysis, e.g. via the reversible addition of thiyl radicals or by ionic catalysis, e.g. with strong protic acids.

Thirdly, this invention relates to the use of vinylic thiophosphorus esters, having a certain, i.e. cis- and transtype, geometric structure. As the main use of such esters, their pesticidal application is described.

2. Prior Art

Vinylic esters of dialkyl phosphoric acid represent an important class of commercial pesticides. (For reference, see pages 40 to 67 of a monograph, entitled "Die Entwicklung neuer insektizider Phosphorsaeure-Ester" by Gerhard Schrader which was published by Verlag Chemie in Weinheim, W. Germany, 1963.)

The biological activity of insecticidal phosphate esters in general is attributed to their inhibition of the cholinesterase enzyme (see pages 6 to 10 of the above referred Schrader monograph). The outstanding pesticidal effectiveness and safety of these esters initiated further research to find even more effective compositions and better methods for their preparation.

Several methods were described in the prior art for the synthesis of vinylic esters of dialkyl dithiophosphoric acids. The method most closely related to the present invention reacted a dialkoxy thiophosphoryl disulfide with a vinylic Grignard or lithium compound, e.g. [for reference, see article by B. Miller in J. Am. Chem. Soc., Vol. 82, page 6205, year 1960]:

$[(C_2H_5O)_2P(S)S]_2 + BrMgCH = CH_2 \rightarrow (C_2H_5O)_2P(S)SCH = CH_2$. The stereochemistry of the reaction was not examined. Apparently, it was assumed that the reaction cannot be used for the stereospecific synthesis of cis- and trans-isomers.

One of the methods for the synthesis of several commercially important vinylic phosphate pesticides, i.e. of carbohydrocarbyloxy propenyl esters of dimethyl phosphoric acids, reacts the sodium derivative of an acetoacetic ester with the corresponding phosphoryl chloride. (For reference, see pages 54 to 59 of the previous reference to Schrader.) An application of this method for the synthesis of a thiono analog is shown by the following reaction scheme:

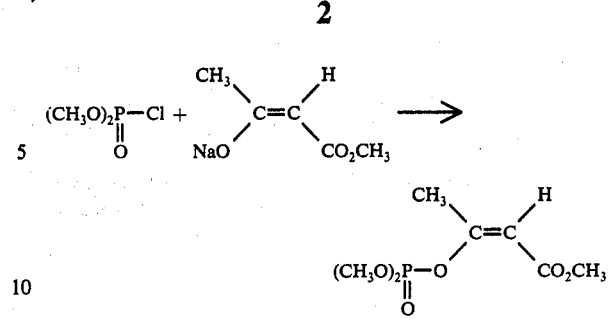

As indicated by the above reaction scheme, this method yields the isomer having the phosphoric and the carboxylic ester groups in cis-configuration to each other. This isomer was found to be biologically less active than the trans-isomer. A slow method of isomerizing the cis- to the trans-isomer by ultraviolet irradiation was disclosed by J. B. Stothers and E. Y. Spencer. (See Can. J. Chem., Vol. 39, page 1389, year 1961). However, no effective method was found in the prior art for the isomerization of vinylic diorgano phosphorus esters. The higher biological activity of the trans-hydrocarbyloxy propenyl esters was attributed to an additional simultaneous interaction of the strongly polar carboxylic acid ester group with a secondary site of the cholinesterase. (For reference, see A. Morello, E. Y. Spencer and A. Vardanis, Biochem. Pharmacol., Vol. 16, pages 1703 to 1710, 1967.) Difference between the activity of cis- and trans-isomers was not known or assumed for those vinylic phosphates which have no polar substituents.

SUMMARY OF THE INVENTION

In the present invention, it was unexpectedly found that cis- and trans-vinylic Grignard and alkali metal compounds retain their configuration when reacted with diorgano phosphoryl disulfides or sulfenyl-chlorides, and yield the corresponding cis- and trans-vinylic esters, respectively.

Furthermore, it was found that thermodynamically unstable cis- or trans-vinylic esters of diorgano phosphorus acids and their isomer mixtures are very effectively isomerized by the reversible addition of free radicals and protons, preferably generated from organic disulfides and strong acids, respectively. Such isomerizations were remarkably free from side reactions such as irreversible addition and hydrolysis.

Lastly, it was discovered that the vinylic esters of specific configuration, which were synthesized via the present novel method, were biologically more active than their geometrical isomers, even though these esters contained no polar substituent.

Process Reactants

In accordance with this invention, cis- and/or trans-esters of diorgano phosphorus acids and isomerized derivatives thereof are prepared in a stereoselective process comprising reacting a corresponding cis- and trans-vinylic metal compound having at least 70% isomer purity, with a diorgano phosphoryl thio compound selected from the group of diorgano phosphoryl disulfides and diorgano phosphoryl sulfenyl chlorides. The cis- and trans-vinylic metal compound reactant is preferably selected from the group of vinylic Grignard, i.e. magnesium chloride, bromide and iodide, and alkali metal compounds. The resulting cis- and/or trans-vinylic ester has at least 70% of the isomer corresponding to the configuration of the vinylic metal reactant. This product can then be isomerized to a thermodynamically stable mixture of geometrical isomers by the reversible addition of species selected from the group of radicals and proton.

Most generally, the reactions of the present process can be schematically represented in the following manner:

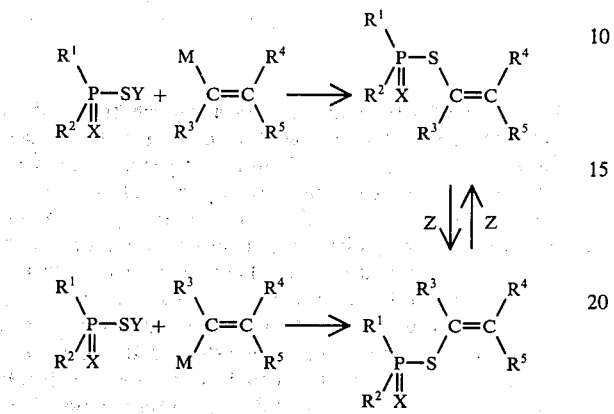

wherein $R^1$ and $R^2$ are organic radicals; $R^3$ and $R^4$ are selected from the group of hydrogen and organic preferably hydrocarbyl radicals; $R^5$ is an organic preferably hydrocarbyl radical which is different from $R^4$; X is sulfur, oxygen, Y is selected from the group of radicals consisting of $R^1R^2P(X)S$, Cl and Br; M is selected from the group of metallic radicals consisting of MgCl, MgBr, Li, Na and K; Z is selected from the group of species consisting of organic thio radicals and protons.

As shown in the above scheme, the diorgano phosphoryl thio compound reactants have the formula:

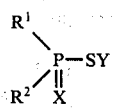

The claimed stereoselective process is basically not dependent on the molecular weight change and similar variations. Nevertheless, somewhat arbitrary limitations and preferences are given by the following description:

(a) $R^1$ and $R^2$ generally include $C_1$ to $C_{30}$ organic radicals having substituents unreactive towards the vinylic metal compound reactant. These organic radicals are preferably selected from the group consisting of hydrocarbyloxy, hydrocarbylthio and hydrocarbyl radicals and monosubstituted derivatives thereof such as alkyloxyalkyl, alkylthioalkyl. The number of carbon atoms in the $R^1$ and $R^2$ radicals is preferably 1–8, more preferably 1–4. $R^1$ and $R^2$ can stand for identical and different organic radicals. If they are identical, it is most preferred that they either be ethoxy or methoxy. If they are different, it is most preferred that $R^1$ be ethoxy or methoxy and $R^2$ be methyl, ethyl or $C_1$ to $C_4$ alkylthio. The suitable organic radicals include aromatic and olefinic radicals and their substituted derivatives such as chlorovinyl, cyanophenyl, etc.

Non-limiting representative examples of suitable $R^1$ and $R^2$ groups include: cetyloxy, hexadecylphenylthio naphthyloxy, methyloxy, ethylthio, propylthio, methyl, propyloxymethyl, phenyl, xylyl, benzylthio, chlorophenylethylthio, ethylsulfonylmethyl, etc.

(b) X is S and O, preferably S.
(c) Y is $R^1R^2P(X)S$ and Cl. In case Y is $R^1R^2P(X)S$, $R^1$, $R^2$ and X are as given above.

Examples of useful phosphoryl disulfides include: dimethoxy thiophosphoryl disulfide, dioctyloxy thiophosphoryl disulfide, dicetyloxy thiophosphoryl disulfide, dichlorophenoxy thiophosphoryl disulfide, didodecylphenyloxy thiophosphoryl disulfide, ethoxy propylthio phosphoryl disulfide, ethyl benzylthio phosphoryl disulfide, propylthiomethoxy ethanethiophosphoryl disulfide, ethyloxy benzenephosphonyl disulfide, dimethyl thiophosphinyl disulfide, methyl phenyl phosphinyl disulfide.

Examples of useful phosphoryl sulfenyl halides include: diethoxy phosphoryl sulfenyl chloride, dihexyloxy phosphoryl sulfenyl chloride, diphenyloxy phosphoryl sulfenyl chloride, ethoxy propylthio phosphoryl sulfenyl chloride, ethoxy ethanephosphonyl sulfenyl chloride.

The vinylic Grignard and alkali metal reactants have the formula:

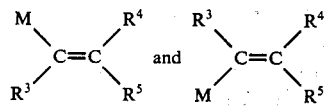

Although the claimed stereoselective process is not molecular weight limited, it is preferred that:

(a) $R^3$ and $R^4$ should be selected from the group consisting of hydrogen and $C_1$ to $C_{30}$ hydrocarbyl radicals and substituted derivatives thereof such as hydrocarbyloxyalkyl, hydrocarbylthioalkyl, hydrocarbylthio, preferably $C_1$ to $C_{30}$ hydrocarbyl radicals. It is more preferred that $R^3$ and $R^4$ be $C_1$ to $C_8$ hydrocarbyl or particularly $C_1$ to $C_5$ alkyl radicals. Most preferably, however, $R^3$ and $R^4$ are hydrogen. The organic radicals can be hydrocarbylthio hydrocarbyloxy, cyanoalkyl and other suitable groups. Preferred examples of nonsubstituted hydrocarbyl radicals are methyl, ethyl, phenyl, benzyl. The hydrocarbyl radicals include mono-substituted radicals such as chlorophenyl, methylsulfonylphenyl.

(b) $R^5$ is a $C_1$ to $C_{30}$ organic radical as above. Preferably, $R_5$ is a $C_1$ to $C_{30}$ hydrocarbyl radical. More preferable ranges for the hydrocarbyl radical are in the $C_1$ to $C_8$ and $C_1$ to $C_5$ ranges. Most preferably, $R^5$ is a $C_1$ to $C_5$ alkyl group.

The exemplary meaning of $R^5$ as an organic radical is the same as those listed for the $R^3$ and $R^4$ groups. However, $R^5$ and $R^4$ should not be identical radicals. The relative steric position of $R^5$ to M is critical in determining the stereochemistry of the reactant and of the product. The structure and stereochemistry of $R^5$ are also important in the application of the product.

(c) M is selected from the group of metallic radicals, consisting of MgCl, MgBr, Li, Na and K. M is preferably MgBr and Li.

A preferred subclass of vinylic metal reactants has the general formula:

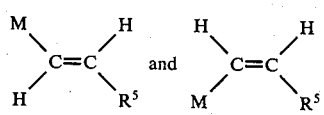

wherein $R^5$ is a $C_1$ to $C_{30}$ hydrocarbyl, preferably a $C_1$ to $C_8$ hydrocarbyl, most preferably a $C_1$ to $C_4$ alkyl radical; and M is MgCl, MgBr, Li, Na and the trans-isomer constitutes at least 70% of the compound.

Examples of useful cis- and trans-vinylic Grignard and alkali metal reactants are: propenyl magnesium chloride, styryl magnesium bromide, 2-butenyl magnesium bromide, hexadecenyl magnesium, bromide, chlorostyryl magnesium bromide, propenyl lithium, 2-chlorophenyl styryl lithium, 2-butenyl lithium, stilbenzyl lithium, 1-phenyl propenyl lithium, 1-chlorophenyl-2-phenyl styryl lithium.

In general, the aliphatic vinyl reagents are preferred. Their reactions are more stereoselective than those of the arylsubstituted reagents. Stereoselective reactions of the alkyl compounds can be carried out under less stringent conditions. Non-hydrocarbon such as ether substituents represent a further possible difficulty for stereoselective reactions. In general, the vinyl reagents should contain at least 70% of either the cis or the trans-isomer to qualify as starting materials for the present stereoselective synthesis.

The cis-/trans- isomerization catalyst, Z, is selected from two groups of reagents having the general formula.

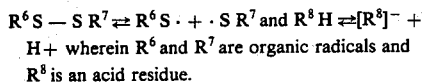

wherein $R^6$ and $R^7$ are organic radicals and $R^8$ is an acid residue.

$R^6$ and $R^7$ are preferably selected from the group of $C_1$ to $C_{30}$ organic radicals more preferably of $C_1$ to $C_8$ organic radicals. Particularly, preferred types of organic radicals are hydrocarbyl radicals and acyl radicals. Non-substituted and substituted aromatic hydrocarbyl radicals and acyl radicals of the structure $R^1R^2P(X)$ are most preferred.

The active free radical type isomerization catalyst species are the thiyl radicals which reversibly add to the double bond of the vinylic ester, e.g.

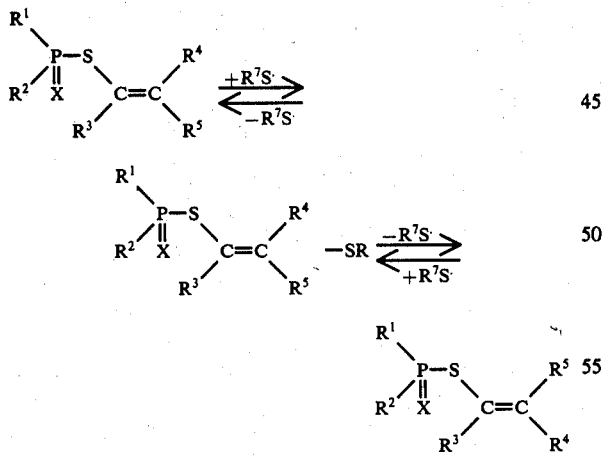

In general, the preferred disulfide isomerization catalysts generate relatively stable thiyl radicals on irradiation and on heating. The diorgano phosphoryl disulfide adding reagents of the present invention can also serve as isomerizing catalysts for the adduct products. Examples of other radical-type isomerization catalysts are as follows: dimethyl disulfide, dicetyl disulfide, dibenzyl disulfide, diphenyl disulfide, dianthryl disulfide, methyl phenyl disulfide, diallyl disulfide, dicarbomethoxymethyl disulfide, diethoxyethyl disulfide, di-3-acetoxypropyl disulfide, di-2-acetylethyl disulfide, etc.

The $R^8$ acid residue radical of the protic acid isomerization catalyst is preferably an inorganic entity. In case $R^8$ is an organic radical, it is preferable that it should contain no more than 8 carbon atoms per acid group. Although the acid used is usually mono-basic, polybasic acids such as polyphosphoric acid and polystyrene-sulfonic acid can be also employed.

The preferred acid-type isomerization catalysts are protic acids having a $pK_a$ greater than or equal to that of the thiophosphorus acid which is applied as a reactant in the form of the disulfide or sulfenyl chloride derivative. In general, the rate of cis-/trans-isomerization is directly dependent on the acid's strength. In the case of protic acids, the isomerization occurs via the reversible addition of protons to the double bond of the vinylic phosphorus esters.

Typical examples of the acids which can be employed are listed in the following: mineral acids, e.g. perchloric, sulfuric, hydrochloric, polyphosphoric; Friedel Crafts catalysts, e.g. boron trifluoride, antimony trichloride; organic acids, e.g. methanesulfonic acid, p-toluenesulfonic acid, trifluoroacetic acid, benzenephosphonic acid. Of the various acid media that can be employed, perchloric acid and boron trifluoride are preferred.

It was surprising to find that when the above ionic catalysts were employed as described, isomerization of the vinylic esters occurred without significant adduct formation and/or acidolysis as side reactions.

The starting cis- or trans-vinylic phosphorus ester materials for the isomerization can be the products of the present stereoselective syntheses. Other vinylic phosphorus esters can be also used. Examples of such esters are 1-carbomethoxy-1-propen-2-yl dimethyl phosphate, 1-dimethylcarbamoyl-1-propen-2-yl dimethyl phosphate, 1-diethylcarbamoyl-1-chloro-1-propen-2-yl dimethyl phosphate, 1-methylcarbamoyl-1-propen-2-yl dimethyl phosphate, 1-carbo-α-methylbenzyloxy-1-propen-2-yl dimethyl phosphate, 1,3-bis-carbomethoxy-1-propen-2-yl dimethyl phosphate, 1-o,p-dichlorophenyl-2-chlorovinyl diethyl phosphate, 1-(2,4,5-trichloro)phenyl-2-chlorovinyl dimethyl phosphate.

In general, suitable starting materials for the present isomerization process can be represented by the general formula:

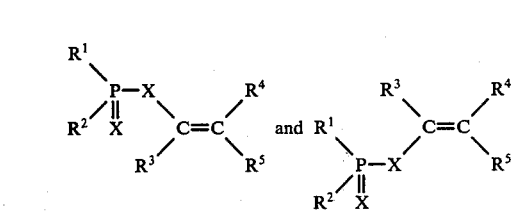

wherein the symbols have the following meaning:
(a) $R^1$ and $R^2$ are $C_1$ to $C_{30}$ organic radicals selected from the group consisting of hydrocarbyloxy, hydrocarbylthio, hydrocarbyl radicals and mono-substituted derivatives thereof. Preferred definitions for $R^1$ and $R^2$ are as previously described.
(b) $R^5$ is chlorine, bromine, fluorine, and a $C_1$ to $C_{30}$ organic radical selected from the group consisting of hydrocarbyl, substituted hydrocarbyl — such as hydrocarbylthioalkyl, chlorinated hydrocarbyl, carbohydrocarbyloxyalkyl — hydrocarbylthio, acyl groups — preferably those derived from carboxylic, diorganophosphorus, sulfonic, carbamic, xanthic acids — acylthio groups preferably those derived from the above acids, cyano. The number of carbon atoms in the organic radicals is limited preferably to 8, more preferably to 5. The type of organic radical is preferably hydrocarbyl more preferably alkyl. $R^5$ must not be identical with $R^4$.

(c) $R^3$ and $R^4$ are hydrogen, chlorine, bromine, fluorine and the same $C_1$ to $C_{30}$ radicals which were listed above for $R^5$. It is, however, preferred that $R^3$ and $R^4$ should be hydrogen, chlorine, cyano, methyl. It is most preferred to have $R^3$ and $R^4$ equal H.

Before the isomerization, these compounds have at least 70% of either the cis- or the trans-isomer. More preferably, the major isomer of the starting material is the thermodynamically less stable one.

PROCESS CONDITIONS

Some of the reactants of the present stereoselective process are unstable. Most of them are not commercially available. As such they are best prepared before use via known methods.

Among the phosphorus reactants the diorgano phosphoryl disulfides are prepared by the oxidation of the corresponding thio acids of phosphorus as described in Volume 12 of the "Houben Weyl" series of monographs, entitled "Methoden der Organischen Chemie," edited by E. Mueller, published by G. Thieme Verlag, Stuttgart, W. Germany, 1963-1964. Phosphoryl sulfenyl chlorides in turn can be prepared by the chlorination of the disulfides according to procedures also given in the above reference book.

The vinylic metal compounds are best prepared from the corresponding cis- and/or trans-vinylic bromides and chlorides. The reaction of metallic magnesium with these halides under mild conditions provides the corresponding cis- and trans-vinylic Grignard reagent with the retention of the reagent's configuration. Vinylic alkali metal reagents can be similarly prepared. As a reference for these preparations, a review article, "Vinyl Compounds of Metals," by Dietmar Seyferth may be used which appeared in the third volume of a series, "Progress in Inorganic Chemistry," edited by F. A. Cotton and published by Interscience in 1962.

A general procedure used for the preparation of the propenyl magnesium bromide isomers is as follows: into a dry, four-necked, 1 liter flask equipped with a dropping funnel, dry ice condenser, air stirrer and thermometer were placed magnesium turnings and enough dry tetrahydrofuran to just cover the metal. To the magnesium tetrahydrofuran mixture was added 5.0 grams of the appropriate pure cis- or trans-1-bromopropene and the mixture stirred until an exothermic reaction was observed. Then, additional cold tetrahydrofuran was added to control the exothermic reaction. Thereafter, cis- or trans-1-bromopropene was added dropwise, as a tretrahydrofuran solution, so as to maintain the reaction temperature between about 50° and about 60° C. When the addition was completed, the reaction was stirred for an additional 30 minutes, filtered, and then used immediately.

The disulfide isomerization catalysts are usually readily derived by the oxidation of the corresponding thiols. The acid catalysts are mostly commercial chemicals.

Stereoselective Synthesis

It was found surprisingly that the reaction of diorgano phosphoryl disulfides and sulfenyl halides with vinyl metal compounds is stereospecific. The stereospecific reaction occurs in the liquid phase. The vinylic metal reagents are preferably used in solvents. These solvents are selected to be inert towards both the metal and the phosphorus reagent. Especially the presence of the vinylic metal reagent limits the choice of solvents. Suitable solvents include ethers such as diethyl ether, tetrahydrofuran, dioxan; hydrocarbons such as pentane, cyclohexane and benzene; and mixtures thereof. A typical reaction may be carried out by slowly adding a liquid thiophosphoryl disulfide to a cooled, stirred solution of cis- or trans-vinylic Grignard compound is tetrahydrofuran.

The stereospecific displacement reaction usually occurs readily on mixing the reagents at room temperature or below. The reaction temperatures can vary between about −150° and about +50° C., preferably between about −90° C. and about +40° C., most preferably between −30° C. and +30° C. The reaction occurs very rapidly even at very low temperatures. Generally, the freezing of the reaction mixture and the costs of refrigeration limit the otherwise desirable cooling. The upper limit of the reaction temperature is determined so as to avoid the isomerization of either the cis- or trans-vinylic metal starting compound or the vinylic dithiophosphate product. The process is normally performed under atmospheric pressures; however, the use of normally gaseous solvents such as dimethyl ether may result in a super-atmospheric process.

The mole ratio of the diorgano phosphoryl derivative to the cis- or trans-vinyl metal reagent is in general close to about 1:1. However, this ratio may be varied over a wide range, and, in general, can be between about 3:1 and about 1:3. The preferred ratio is between about 1.5:1 and about 1:1.5.

In the event a phosphoryl sulfenyl chloride is used as one reactant, an excess of the vinylic compound should be avoided due to the fact that addition of the sulfenyl chloride to the olefinic unsaturation may occur as a side reaction. To avoid such a side reaction, it may be preferable to add the phosphorus compound to the vinylic metal compound. In the case of a thiophosphoryl disulfide, a slow addition to the phosphorus compound is preferred.

Isomerization

The present isomerization process can be carried out with surprisingly little side reaction.

In general, the process for the isomerization of cis- or trans-S-alkenyl dithiophosphates is based upon the reversible selective addition of an electrophilic species such as a cation or a free radical to the olefinic double bond of such compounds. As a cation a proton is a preferred adding agent. Thiyl radicals are suitable free radical isomerization catalysts. When a strong acid such as perchloric acid is used as a hydrogen ion source, isomerization at the olefinic site can be effected without destroying the acid-sensitive phosphate ester part of the molecule. Also, the irradiation of the vinylic dithiophosphate in the presence of a disulfide as a thiyl radical source does not result in any significant adduct formation but, rather, in isomerization.

The mechanism of the isomerization can be depicted by the following scheme:

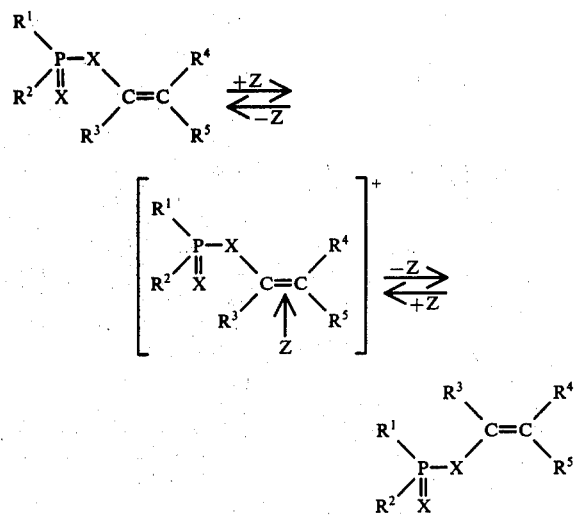

wherein the various symbols have the same meaning as before. The isomerization, however, is not limited to those cis-/trans-isomeric phosphorus esters which can be prepared by the stereospecific process of this invention.

The isomerization takes place preferably in the liquid phase. Since most of the vinylic phosphorus ester starting materials are liquid, solvents are generally absent. Solvents, however, can be beneficially used for radiation energy transfer. The small amount of isomerization catalyst, if solid, is usually soluble in the compound to be isomerized. Gaseous isomerization catalysts are usually also soluble under the reaction conditions. Generally, the reaction mixtures are under atmospheric pressure. However, if necessary, superatmospheric pressures, usually up to 20 atmospheres, may be used.

When the isomerizing species are thiyl radicals, the isomerization proceeds even at very low temperatures. For example, when the thiyl radicals are generated from the corresponding disulfides by ultraviolet radiation, isomerization can occur at −80° C. However, heat can be also used for the partial homolysis of disulfides into thiyl radicals. In such a case temperatures in excess of 100° C. can be used.

Isomerization by strong acids occurs at a highly increased rate when elevated temperatures are used. However, at high temperatures side reactions are much more likely to occur. Therefore, isomerization by acids is much more sensitive to temperatures than disulfide isomerization.

Isomerization temperatures can vary from about −90° C. to about +150° C., more preferably from about 0° to about 100° C., most preferably from 20° to 50° C.

Dependent upon the conditions, the time of ionic and the free radical isomerizations can vary between minutes and days. Sometimes it can be of advantage to effect isomerization upon longer standing at ambient temperatures.

Both the radical and cationic type isomerization catalysts are normally employed in catalytic amounts, i.e. 0.01 to about 10 wt. %, preferably 0.05 to 5 wt. %, of the reaction mixtures.

The radiations which are useful to generate thiyl radicals from disulfides include ultraviolet and visible light, and gamma irradiation. Compounds may be added to the isomerization mixture to help the transfer of radiation energy. For example, the addition of ketones such as acetone can increase the rate of disulfide isomerization on irradiation with ultraviolet light.

The free radical isomerization process is particularly preferred when a predominantly cis-isomer is made by the free radical addition of a dialkyl dithiophosphoric acid to an alkylacetylene. In such a case, after the addition step, which is usually carried out in the presence of radiation, the acetylene can be removed and the residual acid oxidized to the corresponding disulfide. In turn, the disulfide will act as a source of a free radical isomerization catalyst upon irradiation in the next step. In this manner, the direct synthesis and the subsequent isomerization can be economically integrated as is shown by the following three equations:

Addition Step (1)

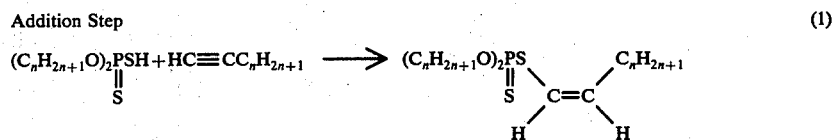

Oxidation Step (2)

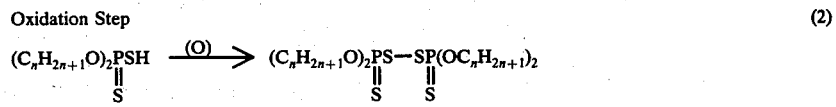

Isomerization Step (3)

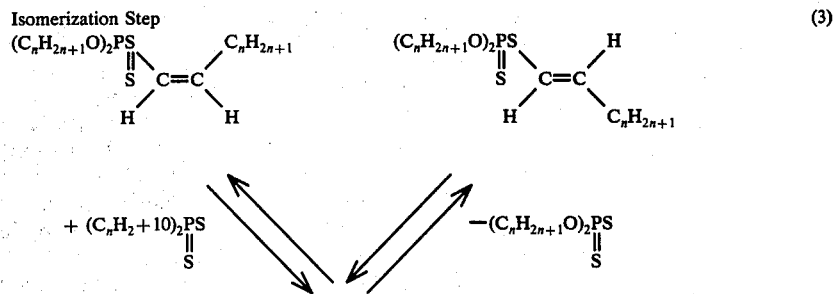

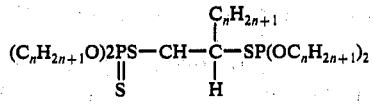

wherein $n = 1\text{–}18$, preferably 1–8, most preferably 1–2.

New Compositions of Matter

The stereospecific displacement and the selective isomerization reactions described in the present invention result in novel compositions.

The displacement reactions yield new compositions of matter of the general formula:

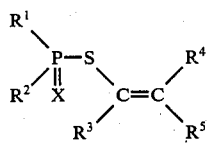 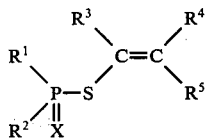

wherein the meaning of $R^1$ to $R^5$ and X is as previously defined, and wherein the composition contains at least 70% of either the cis- or the trans-isomer.

Preferred compositions of matter have the general formula:

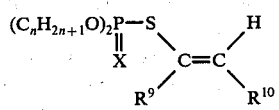

wherein X is S and O; $R^9$ and $R^{10}$ are $C_1$ to $C_8$ hydrocarbyl, preferably $C_1$ to $C_5$ alkyl, more preferably methyl radicals and $n$ is $C_1$ to $C_{18}$, preferably 1–8, most preferably 1–2, and wherein said isomer is at least at its maximum equilibrium concentration or more preferably said isomer constitutes at least 70% of the isomer mixture.

A more specifically-claimed type of the new displacement products has the general formula:

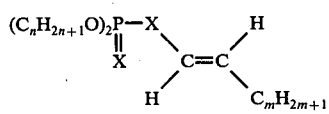

wherein $m$ and $n$ are 1–18, more preferably 1–8, most preferably 1–2, and wherein the trans-isomer shown is present at least at its thermodynamic equilibrium concentration at ambient temperatures. The concentration of the trans-isomer in these new compositions is preferably 70% or higher.

Examples of the claimed trans-composition are: S-1-carbomethoxy-1-propen-2-yl dimethyl thiophosphate, S-1-dimethylcarbamoyl-1-propen-2-yl dimethyl thiophosphate, S-1-diethylcarbamoyl-1-chloro-1-propen-2-yl dimethyl thiophosphate, S-1-methylcarbamoyl-1-propen-2-yl dimethyl thiophosphate, S-1,3-bis-carbomethoxy-1-propen-2-yl dimethyl thiophosphate, S-1-o,p-dichlorophenyl-2-chlorovinyl diethyl thiophosphate, S-styryl dimethyl dithiophosphate, S-dodecenyl dipropyl dithiophosphonate, S-2-butenyl O-ethyl methanedithiophosphonate, S-stilbenyl dibenzyl dithiophosphate, S-1-butenyl dichlorophenyl dithiophosphinate.

As previously noted, the novel compositions of this invention are surprisingly effective as pesticides. They show unexpected advantages not only with respect to related compounds but also in comparison with their respective isomers.

In general, for economical use as pesticides the molecular weight of the present compounds is preferably less than 400. The organic groups of the present diorganothiophosphorus esters have preferably less than 8, more preferably less than 4, carbon atoms.

The preferred geometrical isomer of the present compositions is generally the trans, i.e. the isomer having the two key insecticidal groups of the molecule in trans-position. The primarily important group of these compositions is always the phosphorus. The secondary group is usually the more polar group of the $\beta$-vinylic carbon. This is known from the literature. It was found unexpectedly in the present invention that in the case of $\beta$-monosubstitution, the secondary group can be a non-polar hydrocarbyl group. This hydrocarbyl group is preferably an alkyl group. This alkyl group most preferably is methyl or ethyl

Process for Combatting Pests

The novel S-trans-vinylic phosphorus ester pesticide compositions are active against a variety of pests. They are particularly useful as broad spectrum pesticides, particularly insecticides and miticides. The low molecular weight S-alkenyl phosphorus esters have a systemic mode of action besides a contact insecticidal effect. They are particularly effective as soil insecticides and nematocides. The lower alkenyl diethyl dithiophosphates have an outstanding effect against the corn rootworm.

Data on the effectiveness of cis-/trans-isomeric mixtures of S-propenyl dimethyl and diethyl dithiophosphates as broad spectrum insecticides, miticides and nematocides has been disclosed in our copending patent application Serial No. 518,028 — filed on Jan. 3, 1966 for which divisional applications were filed on Aug. 1, 1968, as Ser. Nos. 763,997 and 763,998, now U.S. Pat. Nos. 3,681,219 and 3,584,127, respectively.

In the present work, products containing mainly the cis- or the trans-isomers of these esters have been prepared. The overall insecticidal potential of these isomers in relation to their mixtures was determined. For such a determination, a standard test for cholinesterase enzyme inhibition was used since phosphate esters are known to act as insecticides via blocking that enzyme.

The results surprisingly showed that the trans-isomers of these dithiophosphates and of the corresponding monothiophosphates are in the order of 1000 times more effective cholinesterase inhibitors than the corresponding cis-compounds. The consistent cholinesterase inhibition data led to the recognition of a new concept: Beta vinylic hydrocarbon monosubstitution in a trans-position to the phosphorus group of S-vinylic phosphorus esters leads to an unexpected increase of pesticidal potential as opposed to substitution in the cis-position. Transsubstitution by lower alkyl groups is particularly effective.

While not all trans-hydrocarbon substituted S-vinylic phosphorus esters are economically attractive as pesticides, the new concept led to the determination of a new desirable structural feature in phosphorus pesticides. The pesticidal potential of known isomeric compositions can now be surprisingly increased by converting them to new isomeric mixtures containing a higher percentage of the more active geometrical isomer.

When used as insecticides, the biologically active ingredients of this invention are preferably formulated with a suitable carrier or diluent or combinations thereof.

The term "carrier" or "diluent" as used herein means a material, which can be inorganic or organic and synthetic or of natural origin, with which the active ingredient of this invention can be mixed to formulate to facilitate its storage, transportation and handling, and application to the insects to be treated. The carrier is preferably biologically and chemically inert, and, as used, can be a solid or a fluid. When solid carriers are used, they are preferably particulate, granular, or pelleted; however, other shapes and sizes of solid carriers can be employed as well. Such preferably solid carriers can be natural occurring materials — although subsequently subject to grinding, sieving, purification, and/or other treatments, including for example, gypsum; tripolite; diatomaceous earth; mineral silicate such as mica, vermiculite, talc, and pyrophyllite; clays of the montmorillonite, kaolinite, or attapulgite group; calcium or magnesium limes; or calcite and dolomite; etc. Carriers produced synthetically, as for example, synthetic hydrosilica oxides and synthetic silicates can also be used, and many proprietary products of this type are available commercially. The carrier can also be an elemental substance such as sulfur or carbon, preferably an activated carbon. If the carrier possesses intrinsic catalytic activity such that it would decompose the active ingredient, it is advantageous to incorporate a stabilizing agent, as for example, polyglycols such as diethylene glycol to neutralize this activity and thereby prevent possible decomposition of the active ingredient.

For some purposes, a resinous or waxy carrier can be used, preferably one which is solvent soluble or thermoplastic, including fusible. Examples of such carriers are natural or synthetic resins such as coumarone resin, resin, copal, shellac, dammar, polyvinyl chloride, styrene polymers and copolymers, a solid grade of polychlorophenol such as is available under the registered trademark "Arochlor", a bitumen, and an asphaltite, a wax, for example, beeswax, or a mineral wax such as paraffin wax or Montan Wax or a chlorinated mineral wax or a microcrystalline wax such as those available under the registered trademark "Microvan Wax". Compositions comprising said resinous or waxy carriers are preferably in granular or pelleted form.

Fluid carriers can be liquids, as for example, water, or an organic fluid, including a liquefied normally vaporous or gaseous material, and can be solvents or non-solvents for the active material. For example, the horticultural petroleum spray oils boiling in the range of from about 275° to about 575° F., or boiling in the range of from about 575° to about 1000° F. and having an unsulfonatable residue of at least about 75% and preferably of at least about 90%, or mixtures of these two types of oils are particularly suitable liquid carriers.

The carrier can be mixed or formulated with the active material during its manufacture or at any stage subsequently. The carrier can be mixed or formulated with the active material in any proportion depending upon the nature of the carrier. One or more carriers, moreover, can be used in combination.

The compositions of this invention can be concentrated, suitable for storage and transport and contain, for example, from about 5 to about 95% by weight of the active ingredient, preferably from about 20 to about 80% by weight. These concentrates can be diluted with the same or different carrier to a concentration suitable for application. The compositions of this invention can also be dilute compositions suitable for application. In general, concentrations of about 0.1 to about 10% by weight of the active material based upon the total weight of the composition, are satisfactory, although lower and higher concentrations can be applied if necessary.

The compositions of this invention can also be formulated as dusts. These comprise an admixture of the active ingredient and a finely powdered solid carrier such as aforedescribed. The powdered carriers can be oiled as treated to improve adhesion to the surface to which they are applied. These dusts can be concentrated, in which case a highly sorptive carrier is preferably used. These require dilution with the same or different finely powdered carrier which can be of lower sorptive capacity to a concentration suitable for application.

The compositions of this invention can also be formulated as wettable powders comprising a major proportion of the active ingredient mixed with a dispersant, i.e., a deflocculating or suspending agent, and, if desired, a finely divided solid carrier and/or a wetting agent. A reactive ingredient can be in particulate form or adsorb the part of a carrier and preferably constitutes at least about 10%, more preferably at least about 35% by weight of the final pesticidal composition. The concentration of the dispersing agent should in general be between about 0.5 and about 5% by weight of the total composition, although larger or smaller amounts can be used if desired.

The dispersing agent used in the composition of this invention can be any substance having definite dispersant, i.e. deflocculating or suspending properties as distinct from wetting properties, although the substances can also possess wetting properties as well.

The dispersant or dispersing agent used can be protective colloids such as gelatin, glue, casein, gums, or a synthetic polymeric material such as polyvinyl alcohol and methyl cellulose, etc. Preferably, however, the dispersants or dispersing agents used are sodium or calcium salts of high molecular weight sulfonic acids, as for example, the sodium or calcium salts of lignin derived from sulfite cellulose waste liquors. The calcium or sodium salt of condensed aryls sulfonic acids, for example, the products known as "Tamol 731", are also suitable.

The wetting agents used can be non-ionic type surfactants, as for example, the condensation products of fatty acids containing at least 12, preferably 16 to 20, carbon atoms in the molecule, or abietic acid or naphthenic acid obtained in the refining of petroleum oil fractions with alkylene oxide such as ethylene oxides or propylene oxides, or with both ethylene oxides/propylene oxides, as, for example, the condensation products of oleic acid and ethylene oxide containing about 6 to 15 ethylene oxide units in the molecule. Other non-ionic wetting agents like polyalkylen polymers, commercially known as "Pluronics" can be used. Partial esters of the above acids with polyhydric alcohols such as glycerol, polyglycerol, sorbitol, mannitol, etc., can also be used.

Suitable anionic wetting agents include the alkali metal salts, preferably sodium salts of sulfuric acid esters or sulfonic acids containing at least 10 carbon atoms in a molecule, for example, the sodium secondary alkyl sulfates, dialkyl sodium sulfosuccinates available under the registered trademark "Teepol", sodium salt of sulfonated castor oil, sodium dodecyl benzene sulfonate, etc.

Granulated or pelleted compositions comprising a suitable carrier having the active ingredient incorporated therein are also included in this invention. These can be prepared by impregnating a granular carrier with a solution of an active ingredient or by granulating a mixture of a finely divided carrier and the active ingredient. The carrier used can contain a fertilizer or a fertilizer mixture, such as for example a superphosphate.

The compositions of this invention can also be formulated as solutions of the active ingredient and an organic solvent or mixtures of solvents, such as, for example, alcohols; ketones, especially acetones; ethers; hydrocarbons; etc.

When the toxicant itself is a liquid, these materials can be sprayed upon the insects without further dilution.

Petroleum hydrocarbon fractions used as solvents should preferably have a flash point of about 73° F., an example of this being a refined aromatic extract of kerosene. Auxiliary solvents such as alcohols, ketones, and polyalkylene glycol ethers and esters can be used in conjunction with these petroleum solvents.

Compositions of the present invention can also be formulated as emulsifiable concentrates which are concentrated solutions or dispersions of the active ingredients in an organic liquid, preferably a water-insoluble organic liquid containing an added emulsifying agent. These concentrates can also contain a proportion of water, for example, 50% by volume, based upon the total composition to facilitate the solution with water. Suitable organic liquids include, e.g., the above petroleum hydrocarbon fractions previously described.

The emulsifying agents generally of the type producing water-in-oil type emulsions which are suitable for applications by low volume spraying, or an emulsifier of the type producing oil-in-water emulsions. Oil-in-water emulsions can be used, producing concentrates which can be diluted with relatively large volumes of water for application by high volume spraying or relatively small volumes of water for low volume spraying. In such emulsions, the active ingredient is preferably in a non-aqueous phase.

The present invention is further illustrated in further detail by the following examples, but it is to be understood that the present invention, in its broadest aspects, is not necessarily limited in terms of the reactants or specific temperatures, residence times, separation techniques, and other process conditions, etc.; or dosage levels, exposure times, test insects used, etc. by which the compounds and/or formulations described and claimed or prepared and/or used.

The reactions, the products claimed and their uses are illustrated by the following examples.

EXAMPLE 1

Preparation of trans-S-Propenyl O,O'-Diethyl Dithiophosphate

To 156 g (0.42 m) of diethoxy thiophosphoryl disulfide, dissolved in 100 ml of dry tetrahydrofuran, was added 285 ml of 1.5 m (0.42 m) Grignard solution prepared from 12 g (0.5 m) magnesium turnings, 60 g trans-1-bromo propene (0.50 m) and enough dry tetrahydrofuran to give a total volume of 335 ml. The addition required 90 minutes and the reaction temperature was maintained at −10° to 0° with a dry-ice isopropanol bath. After the Grignard solution had been added, the reaction mixture was stirred for an additional hour. All volatiles were then removed under aspirator vacuum and the residue poured over 500 g of cracked ice. Ether was used to extract the ice-water mixture and the ether extract dried over anhydrous sodium sulfate. The ether was then removed under aspirator vacuum leaving 56 g of residue which was distilled under reduced pressure to give 11 g (11.5% yield) of the product, b.p. 66°–70° (0.12 mm).

The nmr spectrum of the product showed a 6H triplet centered at 1.04 (nonvinylic methyl groups), a 3H multiplet centered at 1.40 (vinylic methyl group), a 4H multiplet at 4.04 (methylene protons adjacent to oxygen atom), and a broad 2H multiplet from 5.3 to 6.3 (vinyl protons), ppm. A multiplet centered at 1.55 ppm is attributed to the vinylic methyl group of the cis-isomer and represents about 30% of the distilled reaction product based on the nmr integration.

EXAMPLE 2

Preparation of cis-Propenyl O,O'-Diethyl Dithiophosphate

Tetrahydrofuran solutions of 370 g. (1.0 m) of diethoxy thiophosphoryl disulfide and of 187 g (1 m) cis-propenyl magnesium bromide were reacted in the manner described in Example 1. After 3 hours stirring at 25°, the volatile components were removed from the reaction mixture under aspirator vacuum. To the residue was added 750 ml of ether and 250 ml of 4% aqueous hydrochloric acid. The ether layer was then separated, washed with 5% aqueous sodium bicarbonate and dried over anhydrous sodium sulfate. After filtering, the ether was removed under reduced pressure and the 153 g of residue distilled under high vacuum to give 71.5 g (32%) of product, b.p. 70°–72° (0.4 mm).

The nmr spectrum showed a 6H triplet centered at 1.03 ppm (non-vinylic methyl groups), a 3H multiplet centered at 1.55 (vinyl methyl group), a 4H multiplet centered at 4.03 (methylenes adjacent to oxygen atoms), and a 2H multiplet from 5.3 to 6.3 (vinyl protons), ppm. A multiplet centered at 1.4 ppm is attributed to the vinyl methyl group of the trans-isomer and represents about 5% of the distilled product.

EXAMPLE 3

Preparation of cis-Propenyl O,O'-Dimethyl Dithiophosphate

To a solution of 314 g (1.0 m) of dimethoxy thiophosphoryl disulfide in 200 ml of dry tetrahydrofuran was added 1.0 m of freshly prepared Grignard reagent (from cis-1-bromopropene) as a tetrahydrofuran solution at −20° to −10° over 70 minutes. The reaction was then stirred at 25° for 3 hours and the volatiles removed under aspirator vacuum. To the residue was added 750 ml of ether and the mixture was filtered. The filtrate was poured over 500 g of cracked ice and the ether layer separated, washed with 5% aqueous hydrochloric acid, washed with 5% aqueous sodium bicarbonate, and dried over anhydrous sodium sulfate. The ether was removed under aspirator vacuum and the residue, 210 g, distilled under high vacuum to give 175.3 g of the product, b.p. 52° (0.3mm), which is contaminated with 30% trimethyl dithiophosphate. Distillation of 120 g of the distilled mixture afforded 52 g (38% yield) of product shown by nmr to be 90% pure.

The nmr spectrum shows a 6H doublet at 3.42 (methoxy methyl), a 3H multiplet centered at 1.52 (vinyl methyl group), a 2H multiplet from 5.3 to 6.3 (vinyl protons), ppm. A weak multiplet centered at 1.37 ppm is assigned to the trans-isomer and represents less than 10% of the distilled product.

EXAMPLE 4

Preparation of trans-S-Propenyl O,O'-Dimethyl Dithiophosphate

To a solution of 157 g (0.5 m) of dimethoxy thiophosphoryl disulfide in 200 ml of dry tetrahydrofuran was added 0.5 m of freshly prepared Grignard reagent, from 12 g (0.5 m) Mg turnings and 60 g (0.5 m) of trans-1-bromopropene, over 20 minutes at −20° to −10°. The reaction was then stirred at 25° for 2 hours and then all volatiles removed under aspirator vacuum. To the residue was added 600 ml of ether and the ether solution washed first with 5% aqueous hydrochloric acid, then with 5% aqueous sodium bicarbonate and dried over anhydrous sodium sulfate. The ether was removed under aspirator vacuum leaving 106 g of residue which was distilled under high vacuum to yield 58.1 g (22% yield) of product, b.p. 54°-74° (0.5 -1.0 mm) contaminated with 25% trimethyl dithiophosphate.

The nmr spectrum showed a 6H doublet at 3.43 (methoxy methyl protons), and multiplet centered at 1.37 (vinyl methyl protons), and a 2H multiplet from 5.3 to 6.3 (vinyl protons) ppm. A minor multiplet centered at 1.52 ppm is attributed to the cis-isomer and represents less than 25% of the pure reaction product.

EXAMPLE 5

Preparation of cis-Propenyl Diethyl Monothiophosphate

The procedure used in previous example was followed using the same quantities. Distillation afforded 7.3 g (20% yield) of a product, b.p. 62°-66° (0.4 mm) which contains 85% cis-vinyl phosphate.

The nmr spectrum showed a 6H triplet centered at 1.32 (non-vinylic methyl groups), a 3H multiplet centered at 1.80 (vinyl methyl group), a 4H multiplet centered at 4.10 (methylene adjacent to oxygen atoms), and a 2H multiplet from 5.8 to 6.2 (vinyl protons), ppm. A multiplet centered at 1.78 ppm is attributed to the vinyl methyl group of the trans-isomer and represents about 15% of the distilled product.

EXAMPLE 6

Preparation of trans-Propenyl Diethyl Monothiophosphate

The procedure used in Example 1 was followed using 102 g (0.3 m) of diethoxy phosphoryl disulfide and 31.0 g (0.3 m) of cis-propenyl magnesium bromide in tetrahydrofuran. Distillation afforded 7.1 g (19% yield) of 71% trans-product, b.p. 59°-66° (0.12 mm).

The nmr spectrum had a 6H triplet centered at 1.32 (non-vinylic methyl groups), a 3H multiplet centered at 1.78 (vinyl methyl group), a 4H multiplet centered at 4.10 (methylenes adjacent to oxygen atoms), and a 2H multiplet from 5.4 to 6.2 (vinyl protons), ppm. A multiplet centered at 1.80 ppm is attributed to the vinyl methyl group of the cis-isomer and represents about 30% of the distilled product.

EXAMPLE 7

Preparation of trans-S-Hexenyl O-Ethyl Benzenedithiophosphonate

A tetrahydrofuran solution of trans-hexenyl magnesium bromide is added to an equimolar amount of ethoxy benzenethiophosphoryl disulfide in the manner described in Example 1. After the removal of the volatile and water soluble or sensitive components from the mixture, the expected product is obtained as a liquid residue.

EXAMPLE 8

Preparation of S-trans-Propenyl Diphenyl Dithiophosphinate

A diethyl ether solution of trans-propenyl lithium is reacted with an ether solution of equimolar amounts of diphenyl thiophosphoryl disulfide at −10° to yield the above dithiophosphinate.

EXAMPLE 9

Preparation of S-trans-Styryl O,O'-Diethyl Thiophosphate

To a dibutyl ether solution of trans-styryl lithium is added an equimolar amount of diethoxy phosphoryl chloride to form the corresponding trans-thiophosphate.

EXAMPLE 10

Isomerization of cis- and trans-Propenyl O,O'-Diethyl Dithiophosphate with Various Catalysts Into a quartz test tube equipped with a standard taper joint was placed the propenyl dithiophosphate and the catalyst. The tube was then stoppered and placed in a 15° water bath about 15 cm from two 75 watt Hanovia lamps and irradiated. Samples were removed at intervals and analyzed by nmr to obtain the isomer ratios. The results are summarized by the following tabulation:

TABLE I

| Catalyst | | Conc. (mole %) | Temp. (° C.) | Time (hours) | $(C_2H_5O)_2P(S)SCH=CHCH_3$ | |
|---|---|---|---|---|---|---|
| Name | Structure | | | | % Cis- | % Trans- |
| Diphenyl Disulphide | $[\phi S]_2$ | 10 | 15 | 0.0 | 95 | 5 |
| | | | | 1.0 | 60 | 40 |
| | | | | 2.0 | 57 | 43 |
| | | | | 4.0 | 58 | 42 |
| | | 2 | 15 | 0.0 | 95 | 5 |
| | | | | 0.5 | 67 | 33 |
| | | | | 1.0 | 60 | 58 |

TABLE I-continued

| Name | Catalyst Structure | Conc. (mole %) | Temp. (° C.) | Time (hours) | $(C_2H_5O)_2P(S)SCH=CHCH_3$ % Cis- | % Trans- |
| --- | --- | --- | --- | --- | --- | --- |
| | | | | 2.0 | 58 | 42 |
| Diethoxy Thiophosphoryl Disulfide | $[(C_2H_5O)_2PS\!\!-\!\!]_2$ $\|\|$ $S$ | 2 | 15 | 0.0 | 95 | 5 |
| | | | | 0.5 | 62 | 38 |
| | | | | 2.0 | 60 | 40 |
| | | | | 3.0 | 57 | 43 |
| Diphenyl Disulphide | $[\phi S]_2\!\!-\!\!$ | 10 | 15 | 0 | 27 | 63 |
| | | | | 3 | 57 | 43 |
| | | | | 5 | 57 | 43 |
| Dimethyl Disulphide | $CH_3SSCH_3$ | 10 | 15 | 0 | 95 | 5 |
| | | | | 20 | 63 | 37 |
| | | | | 26 | 55 | 45 |
| Perchloric Acid | $HClO_4$ (72% aqueous)* | 5 | 25 | 0.0 | 95 | 5 |
| | | | | 72.0 | 75 | 25 |
| | | | | 96.0 | 65 | 35 |
| (No Catalyst) | (Irradiation only) | 0 | 15 | 26 | 95 | 5 |

*No ultraviolet irradiation used in this experiment.

The results of the tabulation show that both the disulfide and the acid catalysts were effective in isomerizing. The aromatic disulfide, i.e. diphenyl disulfide, and the phosphoryl disulfide were more effective than the aliphatic disulfide, i.e. dimethyl disulfide, and the perchloric acid.

EXAMPLE 11

Isomerization of cis-1-Carbomethoxy-1-propen-2-yl Dimethyl Phosphate

The above phosphate isomer, having the carbomethoxy group in a cis-position relative to the phosphate group, is irradiated in the presence of 2 mole % diphenyl disulfide in the manner described in the previous example to yield a thermodynamic equilibrium mixture containing 70% of the trans-isomer.

EXAMPLE 12

Cholinesterase Inhibition by cis- and trans-S-Propenyl O,O'-Dialkyl Dithiophosphates and Monothiophosphates The insecticidal effectiveness of organophosphorus compounds is generally attributed to their inhibition of the cholinesterase enzyme. This inhibiting potency is usually expressed as the concentration of the compound which will reduce the activity of the enzyme by 50%, i.e. $L_{D50}$. The $L_{D50}$ values of several cis- and trans-S-propenyl dialkyl dithiophosphates were determined to estimate the relative insecticidal potential of the geometric isomer pairs.

Test Method: To a solution of 0.2 unit of bovine cholinesterase in 2.97 ml of a buffer solution containing 11.15 g of disodium hydrogen phosphate dodecahydrate and 1.81 g of potassium dihydrogen phosphate per liter of water, 0.03 ml of a solution of the dithiophosphate adduct in benzene was added. This mixture was then incubated in a water bath at 35° C. for 30 minutes. One ml of a solution containing 100 mg of 5,5'-dithiobis-(2-nitrobenzoic acid), 100 mg of acetylthiocholine iodide, and 75 ml of the above buffer solution in sufficient water to make 200 ml was then added and the mixture again incubated in a water bath at 35° C. for 30 minutes more. The amount of inhibition of bovine cholinesterase was then determined from the absorbance of this solution at 420 millimicrons. By using a series of solutions of the test chemical at various concentrations in acetone, the concentration needed for 50% inhibition was determined.

Since dithiophosphates are generally oxidized in vivo to the corresponding monothiophosphates which are more effective cholinesterase inhibitors, our dithiophosphates were oxidized with peroxide for the in vitro test. The oxidation was carried out with peracetic acid in benzene solution at 75° for 20 minutes. After the removal of the excess peracetic acid, the benzene solution was used for enzyme inhibition as described above.

The median inhibiting concentrations for the cis- and trans-S-propenyl dimethyl and diethyl dithiophosphates are listed in Table II. Data on S-vinyl dimethyl dithiophosphate are also tabulated for comparison.

The results show that trans-S-propenyl dimethyl dithiophosphate has an $L_{D50}$ value 1000 times smaller than the corresponding cis-compound. This means that the trans-dimethyl dithiophosphate is a 1000 times more effective cholinesterase inhibitor. In the case of the S-propenyl diethyl dithiophosphates the data show again that the cholinestearase inhibition efficiency is rising with increasing trans-isomer content. Finally, a comparison of the $L_{D50}$ values of S-vinyl and trans-S-propenyl dimethyl dithiophosphates show that the substitution of the trans-vinylic hydrogen by a methyl group increases the insecticidal potential of the phosphite ester.

The $L_{D50}$ values obtained after the oxidation of the dithiophosphates to the corresponding monothiophosphates are generally smaller. The monothiophosphates are stronger inhibitors than the corresponding dithiophosphates. The trans-monothiophosphates are again much more effective than the corresponding cis-compounds.

EXAMPLE 13

Systemic Miticidal Action of cis- and trans-S-Propenyl Dimethyl Dithiophosphates Although the cholinesterase inhibition data showed a superior effectiveness for the trans-isomer, comparative testing under conditions resembling the actual field use of pesticides was of interest. For this purpose, a systemic pesticide test on mites was chosen as an example.

TABLE II

Comparative Cholinesterase Activity of cis- and trans-Isomers of S-Propenyl Dialkyl Monothio- and Dithiophosphates $$(C_nH_{2n+1}O)_2\underset{\underset{X}{\|}}{P}SCH=CH-C_mH_{2m+1}$$

| Experimental Compound | | | | | | Median Cholinesterase Inhibiting Concentration $L_{D50}$, mole/liter | |
|---|---|---|---|---|---|---|---|
| Identification Example No. (Standard) | Structure | | | Isomer Composition | | | |
| | m | n | X | cis- | trans- | Before Oxidation | After Oxidation |
| 3 | 1 | 1 | S | 95 | 5 | $2.2 \times 10^{-4}$ | $4.1 \times 10^{-5}$ |
|   |   |   |   | 20 | 80 | $2.2 \times 10^{-7}$ | $2.8 \times 10^{-8}$ |
| 2 | 1 | 2 | S | 95 | 5 | $2.5 \times 10^{-3}$ | $1.8 \times 10^{-4}$ |
|   |   |   |   | 58 | 42 | $3.3 \times 10^{-5}$ | $4.4 \times 10^{-6}$ |
| 1 |   |   |   | 20 | 80 | $2.2 \times 10^{-6}$ | $1.6 \times 10^{-7}$ |
| (Reference[a]) | 0 | 1 | S | No iso-merism | | $2.6 \times 10^{-5}$ | $3.1 \times 10^{-6}$ |

[a] Unsubstituted S-vinyl dimethyl dithiophosphate was prepared from vinyl magnesium bromide and dimethoxy thiophosphoryl disulphide.

Test Method: Potted bean plants were infested with the two spotted spider mite. The soil in the pots was then treated by applying 20 ml of aqueous emulsion containing 0.05% of the chemical. The emulsions were prepared by dissolving the cis- and the trans-compound in acetone and dispersing it in distilled water with Triton X-100. (The emulsifier is an alkylaryl polyether alcohol derived from nonylphenol and ethylene oxide). After the application of the test emulsion, the plants were held for 5 days and then the degree of mite control was rated.

Test Results: The evaluation showed that on the plant potted in the soil treated with cis-S-propenyl dimethyl dithiophosphate there were live mites and their nymphs, while the plant treated with the corresponding trans-isomer was completely free from mites and nymphs.

What is claimed is:

1. A composition comprising an isomeric mixture of compounds having at least 70% of the trans-isomer of compounds having the general formula:

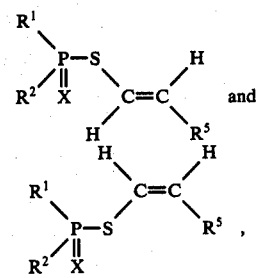

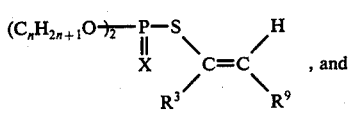

wherein $R^1$ and $R^2$ are $C_1$ to $C_{30}$ hydrocarbyloxy radicals, $R^5$ is a $C_1$ to $C_{30}$ hydrocarbyl radical, and X is O or S.

2. A composition comprising an isomeric mixture of compounds having at least an equilibrium concentration of the trans-isomer of compounds having the general formula:

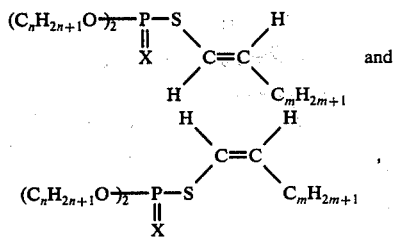

wherein $R^3$ and $R^9$ are $C_1$ to $C_{18}$ hydrocarbyl radicals, $n$ is an integer of 1 to 30, and X is O or S.

3. A composition comprising an isomeric mixture of compounds having at least an equilibrium concentration of the trans-isomer of compounds having the general formula:

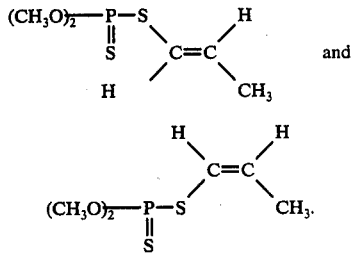

wherein $m$ and $n$ are integers of 1 to 18, and X is O or S.

4. A composition comprising an isomeric mixture of compounds having at least an equilibrium concentration of the trans-isomer of compounds having the formula:

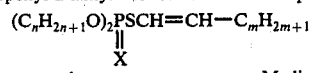

5. A composition comprising an isomeric mixture of compounds having at least an equilibrium concentration of the trans-isomer of compounds having the formula:

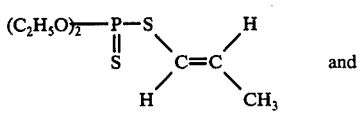

-continued

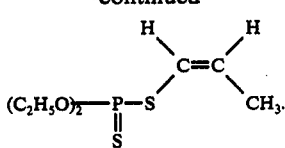

6. A composition comprising an isomeric mixture of compounds having at least 70% of the isomer having the formula:

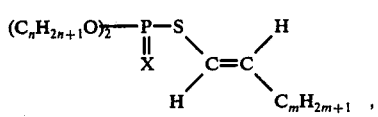

wherein $m$ and $n$ are integers of 1 to 18, and X is O or S.

7. A composition comprising an isomeric mixture of compounds having at least 70% of the isomer having the formula:

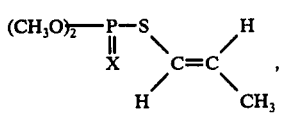

wherein X is O or S.

8. A composition comprising an isomeric mixture of compounds having at least 70% of the isomer having the formula:

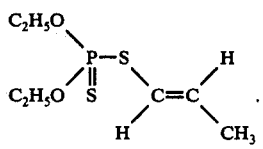

wherein X is O or S.

9. A composition comprising an isomeric mixture of compounds having at least 70% of the isomer having the formula:

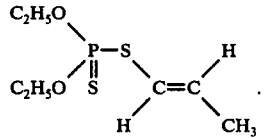

10. A composition comprising an isomeric mixture of compounds having at least 70% of the isomer having the formula:

$$\begin{array}{c} C_2H_5O \\ \phantom{C_2H_5O}\diagdown \\ \phantom{C_2H_5O}P-S \\ \phantom{C_2H_5O}\diagup\| \phantom{S}\diagdown \phantom{C=C}H \\ C_2H_5O \phantom{/}S \phantom{\diagdown}C=C \\ \phantom{C_2H_5O \phantom{/}S \phantom{\diagdown}}H \phantom{C=C}CH_3 \end{array}$$

11. A composition comprising an isomeric mixture of compounds having at least 70% of the isomer having the formula:

$$\begin{array}{c} C_2H_5O \\ \phantom{C_2H_5O}\diagdown \\ \phantom{C_2H_5O}P-S \\ \phantom{C_2H_5O}\diagup\| \phantom{S}\diagdown \phantom{C=C}H \\ C_2H_5O \phantom{/}S \phantom{\diagdown}C=C \\ \phantom{C_2H_5O \phantom{/}S \phantom{\diagdown}}H \phantom{C=C}CH_3 \end{array}$$

* * * * *